United States Patent [19]

Heiba

[11] Patent Number: 4,744,818

[45] Date of Patent: May 17, 1988

[54] HERBICIDAL N-HALO-5(SUBSTITUTED-PHENOXY OR -PYRIDYLOXY)-2-SUBSTITUTED BENZOIC ACID SULFONAMIDES AND SULFAMATES

[75] Inventor: El-Ahmadi I. Heiba, Princeton, N.J.

[73] Assignee: Rhone-Poulenc Agrochimie, Lyone, France

[21] Appl. No.: 286,935

[22] Filed: Jul. 27, 1981

[51] Int. Cl.[4] .................. A01N 43/40; A01N 41/10; C07D 239/72; C07C 147/107

[52] U.S. Cl. ......................................... 71/94; 71/103; 546/286; 546/287; 546/288; 546/291; 558/413; 558/437; 560/12; 560/13; 562/430; 260/513.6; 260/543 A

[58] Field of Search ............... 71/103, 94; 546/286, 546/287, 288, 291; 260/543 A, 513.6, 465 D; 560/12, 13; 562/430; 558/413, 437

[56] References Cited

U.S. PATENT DOCUMENTS

| | | | |
|---|---|---|---|
| 3,137,563 | 6/1964 | Newcomer et al. | 71/118 |
| 3,147,219 | 9/1964 | Paterson | 260/543 A |
| 3,282,991 | 11/1966 | Klein et al. | 560/103 |
| 3,322,525 | 5/1967 | Martin et al. | 71/98 |
| 3,368,953 | 2/1968 | Petterson | 204/158 |
| 3,452,091 | 6/1969 | Petterson | 260/556 |
| 3,454,637 | 7/1969 | Petterson | 260/556 |
| 3,784,635 | 1/1974 | Theissen | 560/21 |
| 3,983,168 | 9/1976 | Theissen | 71/111 |
| 4,063,929 | 12/1977 | Bayer et al. | 71/111 |
| 4,285,723 | 8/1981 | Cartwright et al. | 564/99 |

FOREIGN PATENT DOCUMENTS

| | | |
|---|---|---|
| 0003416 | 8/1979 | European Pat. Off. . |
| 0023392 | 2/1981 | European Pat. Off. . |
| 0030676 | 6/1981 | European Pat. Off. . |
| 0062637 | 6/1974 | Japan . |

OTHER PUBLICATIONS

Varma et al. *India J. Chem.* vol. 4, pp. 445–446 (1966).

Primary Examiner—Donald B. Moyer
Assistant Examiner—L. Hendriksen
Attorney, Agent, or Firm—Morgan & Finnegan

[57] ABSTRACT

N-halo-5-(substituted-phenoxy or -pyridyloxy)-2-substituted benzoic acid sulfonamides and sulfamates, their preparation and use as herbicides are disclosed.

16 Claims, No Drawings

HERBICIDAL N-HALO-5(SUBSTITUTED-PHENOXY OR -PYRIDYLOXY)-2-SUBSTITUTED BENZOIC ACID SULFONAMIDES AND SULFAMATES

BACKGROUND OF THE INVENTION

Herbicidal 5-[2-chloro-4-(trifluoromethyl)phenoxy]-2-nitrobenzoic acid and salts thereof, and various herbicidal derivatives of these compounds have been proposed including alkyl and cycloalkyl esters, alkylthio esters, phenyl ester, alkyl and dialkyl amido and benzoyl chloride forms. U.S. patents which describe such compounds and the like include U.S. Pat. Nos. 3,652,645; 3,784,635; 3,873,302; 3,983,168; 3,907,866; 3,798,276; 3,928,416; and 4,063,929. Published European Applications 3416 and 23,392 disclose N-sulphonyl-3-phenoxy-benzamide derivatives and their salts as herbicides.

SUMMARY OF THE INVENTION

This invention relates to herbicidal compounds of the formula:

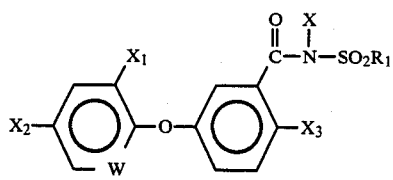

wherein $R_1$ is OM; substituted or unsubstituted hydrocarbyl; (e.g., having from 1 to 12 carbon atoms), substituted or unsubstituted phenyl; or substituted or unsubstituted heterocycle, (e.g., having from 5 to 7 ring atoms).

Examples of $R_1$ include $C_1$–$C_4$ alkyl; $C_1$–$C_4$ alkyl substituted with one or more, preferably no more than 4, of aryl, (particularly phenyl), Cl, Br, OH, O alkyl ($C_1$–$C_4$), SH, S alkyl ($C_1$–$C_4$), COOH, COO alkyl ($C_2$–$C_5$), CN, etc.; $C_2$–$C_6$ alkenyl; $C_2$–$C_6$ alkynyl; and aryl, particularly phenyl; or aryl substituted with one or more, preferably no more than 4, of Cl, Br, alkyl ($C_1$–$C_4$), CN, COOH, COO alkyl ($C_2$–$C_5$), $NO_2$, OH, O alkyl ($C_1$–$C_4$), SH, S alkyl ($C_1$–$C_4$), etc.;

W is CH, C-$X_4$ or N;

M is an agronomically acceptable cation such as an alkali metal, ammonium or substituted ammonium cation;

X is halogen, preferably chlorine;

W is CH, $CX_4$ or N;

$X_1$, $X_2$, $X_3$ and $X_4$, are substituents capable of imparting herbicidal properties. Suitable substituents include halogen, such as F, Cl, and Br; polyhaloalkyl, such as $CF_3$; $NO_2$; CN; alkyl; alkoxy; $SO_2$ alkyl; $SO_2NH_2$; NO; COO alkyl and the like in which the alkyl and alkoxy groups preferably contain 1 to 4 carbon atoms.

Compounds in which $X_1$ is Cl, $X_2$ is $CF_3$ and W is CH are preferred.

A preferred compound has the Formula I in which X is Cl, $X_1$ is Cl, $X_2$ is $CF_3$, $X_3$ is $NO_3$, W is CH, and $R_1$ is methyl.

The compounds of this invention can be easily prepared by methods known in the art. For example the compounds in which X is halogen and $R_1$ is substituted or unsubstituted hydrocarbyl, phenyl, or a heterocycle are prepared from the known precursors in which X is hydrogen by reaction with a hypohalite salt as shown in Examples 1 and 2. Precursors in which X is hydrogen are known and are described in European Published Applications 3416 and 23,392 which are incoporated herein by reference in their entirety.

Similarly, t-butylhypochlorite or $Cl_2O$ can be used as the halogenating agent.

The sulfamates of Formula I (in which $R_1$ is OM) are prepared from the corresponding aryloxy benzoic acid amide by reaction with $SO_3$ and an amine, e.g., a tertiary amine; and subsequent introduction of the halogen as disclosed above. Also, the aryloxy benzoic acid chloride can be reacted with sulfamic acid and tertiary amine, and converted to the halo derivative as disclosed above.

The compounds of this invention are superior selective herbicides, with both pre- and post-emergence activity. Among the crops on which the herbicides of this invention could be advantageously employed are, for example, cotton, soybeans, rice, peanuts, corn and cereal crops.

The herbicidal compounds of this invention can be applied in any amount which will give the required control of weeds. A preferred rate of application of this invention is from about 0.1 to about 2 pounds per acre.

The herbicides described herein can be applied to the growth medium, to the plants or incorporated in the soil, either by itself, or as is generally done, as a component in a herbicidal composition or formulation which also comprises an agronomically acceptable carrier. By an agronomically acceptable carrier is meant any substance which can be used to dissolve, disperse, or diffuse a herbicidal component in the composition without impairing the effectiveness of the herbicidal compound and which by itself has no detrimental effect on the soil, equipment, crops or agronomical environment. The herbicidal composition of this invention can be either solid or liquid formulations or solutions.

The compounds of this invention can be dissolved in any appropriate solvent but the preferred solvent is water. The concentration of the solution can vary from about 2% to about 80% with a preferred range of about 25% to about 75%.

This invention is illustrated by the following examples.

EXAMPLE 1

Preparation of N-chloro-5-[2,4-dichloro phenoxy]-2-nitro-N-methanesulfonyl benzamide 5-[2,4-dichloro phenoxy]-2-nitro-N-methanesulfonyl benzamide (0.5 g M.W. 405; m.p. 181° C.) was dissolved in 20 ml. of "Clorox" solution (aqueous NaClO). The solution was stirred at room temperature for 30 minutes. Acetic acid was added dropwise until pH=7.5 and the reaction mixture was stirred for an additional 30 minutes. The precipitate was filtered, washed with cold water, and air dried to yield 0.5 g of the named compound m.p. 161°–163° C.

Unlike the starting material, the N-chloro derivative is soluble in $CCl_4$ and not soluble in cold basic solutions. It liberates $I_2$ from KI and the determination of the liberated $I_2$ by titration with sodium thiosulfate gave a molecular weight of approximately 440. Its mixed melting point with the starting material 145°–154° C. IR band at 1728 (strong C=O band) compared with an IR band at 1688 for the starting material.

EXAMPLE 2

Preparation of N-chloro-5-[2-chloro-4-(trifluoromethyl)phenoxy]-2-nitro-N-methanesulfonyl benzamide 5-[2-chloro-4-(trifluoromethyl)phenoxy]-2-nitro-N-methanesulfonyl benzamide, m.p. 215°–218° C. was chlorinated with "Clorox" (aqueous NaClO), following procedure I, to yield a product, m.p. 160°–161° (crystallizes from chloroform/ether).

The product liberates $I_2$ from KI, has no N-H band in the NMR and has a strong, =C=O absorption band in the IR at 1728.

EXAMPLE 3

The compound of Example 2 was tested for herbicidal activity in the following manner.

Crop and weed species are planted in 10"×12" disposable fiber flats containing sterilized field soil to provide each flat with a minimum 2" row of all test species. Crop species consist of field corn (CN), cotton (CT), wheat (WT), rice (RI) and soybeans (SB). The weed species consist of barnyardgrass (BYG), giant foxtail, (GTF), crabgrass (CG), velvetleaf (VL), cocklebur (CB), wild mustard (WM), pigweed (PW), and annual morningglory (MG), and prickly sida (PS). Cotton, corn, soybean, wheat, rice, morningglory, and cocklebur plantings consist of 4 to 5 seeds per row depending upon species. The smaller seeded species (velvetleaf, wild mustard, pigweed, prickly sida, crabgrass, barnyardgrass and green foxtail) are planted in an uncounted but sufficient number to provide a solid row of seedlings.

A light initial watering is done from the top immediately after treatment for preemergence flats. Plantings for the pre-emergence phase are made not more than one day in advance of treatment.

Three seeds of cocklebur (CB), soybean (SB), and cotton (CT) are planted in 2" pots of potting mix about 2 weeks before treatment. All pots are thinned to one uniform plant of each species for each treatment before herbicide treatment. Corn (CN), wheat (WT), rice (RI), wild oats (WO), barnyardgrass (BYG), crabgrass (CG), giant foxtail (GIF), annual morningglory (MG), wild mustard (WM), velvet leaf (VL), pigweed (PW), and prickly sida (PS) are planted in minimum of 2" rows in a 6"×10" fiber flat of field soil. Plantings are made 10 to 14 days prior to treatment so as to provide plants of the proper stage of development at time of treatment.

The desired stage of development for treatment of the post-emergence broadleaf species (CT, SB, CB, VL, WM, PW) is the one true leaf or first trifoliate leaf stage. The desired stage for corn would be a height of 3–4", while a 1" height would be adequate for the grasses.

Spray applications are made with an air pressurized track sprayer using a single 80015E Tee fit nozzle at 36 psi, delivering 40 gal/A. Chemicals are sprayed simultaneously to one flat of established plants and one pot each of soybeans, cotton and cocklebur for the post-emergence phase and one newly seeded flat for the pre-emergence phase. Application is made in a solvent mixture consisting of 20 ml acetone and 20 ml water and a surfactant concentration of 0.1 percent.

Following spray application, flats are returned to the greenhouse where all watering is done only by subirrigation except in the pre-emergence phase which is lightly top watered by sprinkling when first placed in the greenhouse.

Two weeks after treatment, the pre- and post-emergence injury and control is rated in a 0–100 percent injury and control scale. Special physiological effects are rated as to intensity also at this time.

The herbicidal test data is reported for the compound of Example 2 of the present invention. The following lists metric equivalents for rates expressed in terms of lbs./acre.

| Application Rate | |
|---|---|
| US - lb./acre | Metric - kg/ha |
| 10.0 | 11.2 |
| 4.0 | 4.48 |
| 2.0 | 2.24 |
| 1.0 | 1.12 |
| 0.5 | 0.56 |
| 0.25 | 0.28 |
| 0.125 | 0.14 |
| 0.0625 | 0.07 |

Test results are set forth in the Table.

TABLE

| Rate* | BYG | GTF | CG | VL | CB | WM | PW | MG | PS | CT | CN | SB | RT | WT |
|---|---|---|---|---|---|---|---|---|---|---|---|---|---|---|
| (PRE) | | | | | | | | | | | | | | |
| 1 | 10 | 9 | 10 | 10 | — | 10 | 10 | 10 | 10 | 2 | 4 | 1 | 9 | 5 |
| ½ | 10 | 10 | 10 | 10 | — | 10 | 10 | 10 | 10 | 3 | 3 | 1 | 8 | 10 |
| ¼ | 10 | 10 | 10 | 10 | — | 10 | 10 | 6 | 10 | 4 | 3 | 0 | 9 | 6 |
| ⅛ | 5 | 6 | 9 | 9 | — | 10 | 10 | 2 | 8 | 1 | 2 | 0 | 7 | 2 |
| (POST) | | | | | | | | | | | | | | |
| 1 | 7 | 7 | 6 | 10 | 10 | 10 | 9 | 8 | 6 | 9 | 0 | 2 | 3 | 3 |
| ½ | 3 | 7 | 6 | 9 | 10 | 10 | 9 | 8 | 5 | 9 | 0 | 3 | 2 | 3 |
| ¼ | 2 | 5 | 6 | 7 | 9 | 10 | 9 | 8 | 2 | 9 | 0 | 1 | 0 | 1 |
| ⅛ | 2 | 2 | 2 | 6 | 10 | 10 | 9 | 5 | 2 | 9 | 0 | 1 | 0 | 1 |

*Rate is in pounds per acre

Although the present invention has been described with reference to preferred embodiments, it is to be understood that modifications and variations may be resorted to, without departing from the spirit and scope of this invention, as those skilled in the art will readily understand. Such modifications and variations are considered to be within the purview and scope of the appended claims.

I claim:

1. A compound having herbicidal activity of the formula:

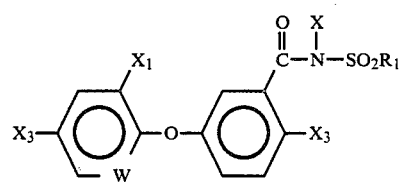

(i) W is CH, C-$X_4$ or N;

(ii) $R_1$ is $C_2$ to $C_6$ alkenyl; $C_2$ to $C_6$ alkynyl; $C_1$-$C_4$ alkyl substituted with up to 4 substituents selected from the group consisting of phenyl, Cl, Br, OH, O alkyl of 1 to 4 carbon atoms, SH, S alkyl of 1 to 4 carbon atoms, and CN; or phenyl substituted with up to 4 substituents selected from the group consisting of Cl, Br, $C_1$ to $C_4$ alkyl, CN, COOH, COO alkyl of 2 to 5 carbon atoms, $NO_2$, OH, O alkyl of 1 to 4 carbon atoms, SH and S alkyl of 1 to 4 carbon atoms;

(iii) X is halogen;

(iv) $X_1$, $X_2$, $X_3$ and $X_4$ are selected from the group consisting of halogen, polyhaloalkyl, $NO_2$, CN, alkyl, alkoxy, $SO_2$ alkyl, $SO_2NH_2$, NO, and COO alkyl, wherein said alkyl and alkoxy groups have 1 to 4 carbon atoms.

2. A compound according to claim 1 in which
W is CH or $CX_4$;
$X_1$, $X_2$ and $X_3$ are halogen, polyhaloalkyl, $NO_2$, CN, alkyl, $SO_2$ alkyl, alkoxy, $SO_2NH_2$, NO, COO alkyl, or COOH in which said alkyl and alkoxy groups contain 1 to 4 carbon atoms; and
$X_4$ is halogen.

3. A compound of claim 1 in which $X_1$ is Cl; $X_2$ is $CF_3$; $X_3$ is $NO_2$; and W is CH.

4. A coupound according to claim 3 in which $R_1$ is $C_2$-$C_6$ alkenyl.

5. A compound according to claim 3 in which $R_1$ is $C_2$-$C_6$ alkynyl.

6. A compound according to claim 3 in which $R_1$ is $C_1$ to $C_4$ alkyl substituted with up to 4 substituents selected from the group consisting of phenyl, Cl, Br, OH, O alkyl of 1 to 4 carbon atoms, SH, S alkyl of 1 to 4 carbon atoms, and CN.

7. A compound according to claim 3 in which $R_1$ is phenyl substituted with up to 4 substituents selected from the group consisting of Cl, Br, $C_1$ to $C_4$ alkyl, CN, COOH, COO alkyl of 2 to 5 carbon atoms, $NO_2$, OH, O alkyl of 1 to 4 carbon atoms, SH, and S alkyl of 1 to 4 carbon atoms.

8. A compound of claim 3 in which X is Cl and $R_1$ is $C_1$-$C_4$-alkyl.

9. A compound according to claim 8 in which $R_1$ is methyl.

10. A compound according to claim 1 in which W is CH, and $R_1$ is $C_2$-$C_6$ alkenyl; $C_2$ to $C_6$ alkynyl; $C_1$ to $C_4$ alkyl substituted with up to 4 substituents selected from the group consisting of phenyl, Cl, Br, OH, O alkyl of 1 to 4 carbon atoms, SH, S alkyl of 1 to 4 carbon atoms, and CN; or phenyl substituted with up to 4 substituents selected from the group consisting of Cl, Br, $C_1$ of $C_4$ alkyl, CN, COOH, COO alkyl to 2 to 5 carbon atoms, $NO_2$, OH, O alkyl of 1 to 4 carbon atoms, SH, and S alkyl of 1 to 4 carbon atoms.

11. A compound having herbicidal activity of the formula:

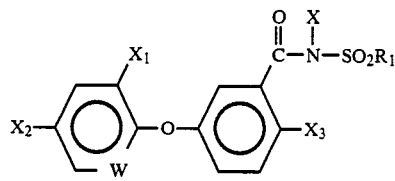

in which W is CH, $R_1$ is OM and M is an alkali metal cation, X is halogen, and $X_1$, $X_2$ and $X_3$ are selected from the group consisting of halogen, polyhaloalkyl, $NO_2$, CN, alkyl, alkoxy, $SO_2$ alkyl, $SO_2NH_2$, NO and COO alkyl wherein said alkyl and alkoxy groups having 1 to 4 carbon atoms.

12. A compound having herbicidal activity of the formula:

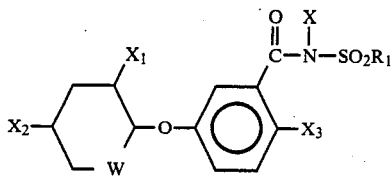

in which W is CH, $R_1$ is OM and M is an ammonium or substituted ammonium cation, X is halogen, and $X_1$, $X_2$ and $X_3$ are selected from the group consisting of halogen, polyhaloalkyl, $NO_2$, CN, alkyl, alkoxy, $SO_2$ alkyl, $SO_2NH_2$, NO and COO alkyl wherein said alkyl and alkoxy groups have 1 to 4 carbon atoms.

13. A compound having herbicidal activity of the formula:

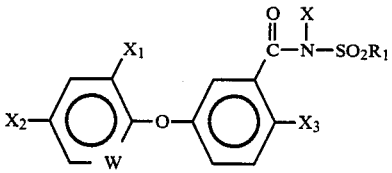

in which $R_1$ is OM and M is an alkali metal cation, $X_1$ is Cl, $X_2$ is $CF_3$, $X_3$ is $NO_2$, W is CH and X is halogen.

14. A compound having herbicidal activity of the formula:

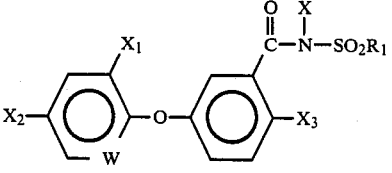

in which $R_1$ is OM and M is an ammonium or substituted ammonium cation, $X_1$ is Cl, $X_2$ is $CF_3$, $X_3$ is $NO_2$, W is CH and X is halogen.

15. A herbicidal composition comprising a herbicidally effective amount of a compound according to claim 1 and an agronomically acceptable carrier.

16. A method of killing weeds in a crop field containing the same which comprises contacting said weeds or their environment with a herbicidally effective amount of a compound according to claim 1.

* * * * *